(12) United States Patent
Roe (10) Patent No.: US 7,670,301 B2
(45) Date of Patent: Mar. 2, 2010

(54) INTEGRATED DISPOSABLE FOR AUTOMATIC OR MANUAL BLOOD DOSING

(75) Inventor: Jeffrey N. Roe, San Ramon, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/950,457

(22) Filed: Dec. 5, 2007

(65) Prior Publication Data
US 2008/0161724 A1 Jul. 3, 2008

Related U.S. Application Data

(63) Continuation of application No. 10/840,931, filed on May 7, 2004, now Pat. No. 7,322,942.

(51) Int. Cl.
*A61B 5/00* (2006.01)
*A61B 17/14* (2006.01)
*A61B 17/32* (2006.01)
*B65D 81/00* (2006.01)

(52) U.S. Cl. .................. 600/583; 600/584; 600/573; 606/181

(58) Field of Classification Search ............... 600/583, 600/584, 573; 606/181, 182
See application file for complete search history.

(56) References Cited

U.S. PATENT DOCUMENTS

| | | | |
|---|---|---|---|
| 1,328,459 A | 1/1920 | Smith | |
| 2,359,550 A | 10/1944 | Eriksen | |
| 2,646,799 A | 7/1953 | Jacoby, Jr. | |
| 2,801,633 A | 8/1957 | Ehrlich | |
| 3,802,842 A | 4/1974 | Lange et al. | |
| D234,644 S | 3/1975 | Sugiyama et al. | |
| 4,061,468 A | 12/1977 | Lange et al. | |
| D249,499 S | 9/1978 | LeRose | |
| D254,444 S | 3/1980 | Levine | |
| 4,203,446 A | 5/1980 | Hofert et al. | |
| 4,325,388 A | 4/1982 | Bucalo | |
| 4,360,016 A | 11/1982 | Sarrine | |
| 4,375,815 A | 3/1983 | Burns | |
| 4,462,405 A | 7/1984 | Ehrlich | |

(Continued)

FOREIGN PATENT DOCUMENTS

EP 1 281 352 A1 2/2003

(Continued)

OTHER PUBLICATIONS

Copending Chinese Patent Application 200580014261.8 Office Action (translated) mailed Apr. 25, 2008.

(Continued)

*Primary Examiner*—Max Hindenburg
*Assistant Examiner*—H. Q. Nguyen
(74) *Attorney, Agent, or Firm*—Woodard, Emhardt, Moriarty, McNett & Henry LLP (57) ABSTRACT

An integrated sampling device defines a first opening and a second opening. The first opening is connected to a channel for drawing fluid automatically towards a test media upon incision by an incision portion. The second opening is positioned over the test media allowing manual sampling of fluid if the channel fails to draw a sufficient amount of fluid onto the test media.

24 Claims, 6 Drawing Sheets

U.S. PATENT DOCUMENTS

| | | |
|---|---|---|
| 4,469,110 A | 9/1984 | Slama |
| 4,490,465 A | 12/1984 | Limbach et al. |
| 4,627,445 A | 12/1986 | Garcia et al. |
| 4,637,403 A | 1/1987 | Garcia et al. |
| 4,653,513 A | 3/1987 | Dombrowski |
| 4,677,979 A | 7/1987 | Burns |
| 4,787,398 A | 11/1988 | Garcia et al. |
| 4,869,249 A | 9/1989 | Crossman et al. |
| 4,895,147 A | 1/1990 | Bodicky et al. |
| 4,924,879 A | 5/1990 | O'Brien |
| 4,990,154 A | 2/1991 | Brown et al. |
| 5,035,704 A | 7/1991 | Lambert et al. |
| 5,100,391 A | 3/1992 | Schutte et al. |
| 5,108,889 A | 4/1992 | Smith et al. |
| 5,304,193 A | 4/1994 | Zhadanov |
| 5,423,847 A | 6/1995 | Strong et al. |
| 5,511,558 A | 4/1996 | Shepard et al. |
| 5,540,709 A | 7/1996 | Ramel |
| 5,545,173 A | 8/1996 | Herbst |
| 5,582,184 A | 12/1996 | Erickson et al. |
| 5,607,401 A | 3/1997 | Humphrey |
| 5,607,437 A | 3/1997 | Simon et al. |
| 5,613,978 A | 3/1997 | Harding |
| 5,628,764 A | 5/1997 | Schraga |
| 5,628,765 A | 5/1997 | Morita |
| 5,680,872 A | 10/1997 | Sesekura et al. |
| 5,730,753 A | 3/1998 | Morita |
| RE35,803 E | 5/1998 | Lange et al. |
| 5,755,733 A | 5/1998 | Morita |
| 5,776,157 A | 7/1998 | Thorne et al. |
| 5,776,719 A | 7/1998 | Douglas et al. |
| 5,798,031 A | 8/1998 | Charlton et al. |
| 5,824,491 A | 10/1998 | Priest et al. |
| 5,830,225 A | 11/1998 | Detsch |
| 5,857,983 A | 1/1999 | Douglas et al. |
| 5,871,494 A | 2/1999 | Simons et al. |
| 5,873,887 A | 2/1999 | King et al. |
| 5,879,311 A | 3/1999 | Duchon et al. |
| 5,916,230 A | 6/1999 | Brenneman et al. |
| 5,931,846 A | 8/1999 | Simon et al. |
| 5,951,492 A | 9/1999 | Douglas et al. |
| 5,951,493 A | 9/1999 | Douglas et al. |
| 5,962,215 A | 10/1999 | Douglas et al. |
| 5,964,718 A | 10/1999 | Duchon et al. |
| 5,971,941 A | 10/1999 | Simons et al. |
| 5,984,940 A | 11/1999 | Davis et al. |
| 5,997,561 A | 12/1999 | Bocker et al. |
| 6,022,366 A | 2/2000 | Schraga |
| 6,036,924 A | 3/2000 | Simons et al. |
| 6,045,567 A | 4/2000 | Taylor et al. |
| 6,048,352 A | 4/2000 | Douglas et al. |
| 6,056,701 A | 5/2000 | Duchon et al. |
| 6,066,103 A | 5/2000 | Duchon et al. |
| 6,071,250 A | 6/2000 | Douglas et al. |
| 6,071,294 A | 6/2000 | Simons et al. |
| 6,086,545 A | 7/2000 | Roe et al. |
| 6,099,484 A | 8/2000 | Douglas et al. |
| 6,143,164 A | 11/2000 | Heller et al. |
| 6,156,050 A | 12/2000 | Davis et al. |
| 6,156,051 A | 12/2000 | Schraga |
| 6,159,424 A | 12/2000 | Kauhaniemi et al. |
| 6,183,489 B1 | 2/2001 | Douglas et al. |
| 6,210,421 B1 | 4/2001 | Bocker et al. |
| 6,270,637 B1 | 8/2001 | Crismore et al. |
| 6,283,982 B1 | 9/2001 | Levaughn et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,346,114 B1 | 2/2002 | Schraga |
| 6,352,514 B1 | 3/2002 | Douglas et al. |
| 6,364,890 B1 | 4/2002 | Lum et al. |
| 6,409,740 B1 | 6/2002 | Kuhr et al. |
| 6,419,661 B1 | 7/2002 | Kuhr et al. |
| 6,561,989 B2 | 5/2003 | Whitson |
| 6,969,359 B2 | 11/2005 | Duchon et al. |
| 2001/0027327 A1 | 10/2001 | Schraga |
| 2001/0039387 A1 | 11/2001 | Rutynowski et al. |
| 2002/0002344 A1 | 1/2002 | Douglas et al. |
| 2002/0004196 A1 | 1/2002 | Whitson |
| 2002/0016006 A1 | 2/2002 | Wendelbro et al. |
| 2002/0029059 A1 | 3/2002 | Purcell |
| 2002/0040230 A1 | 4/2002 | Kuhr et al. |
| 2002/0082522 A1 | 6/2002 | Douglas et al. |
| 2002/0103499 A1 | 8/2002 | Perez et al. |
| 2002/0130042 A1 | 9/2002 | Moerman et al. |
| 2002/0177763 A1 | 11/2002 | Burns et al. |
| 2002/0177788 A1 | 11/2002 | Hodges et al. |
| 2002/0188223 A1 | 12/2002 | Perez et al. |
| 2002/0188224 A1 | 12/2002 | Roe et al. |
| 2003/0050573 A1 | 3/2003 | Kuhr et al. |
| 2003/0060730 A1 | 3/2003 | Perez |
| 2003/0083685 A1 | 5/2003 | Freeman et al. |
| 2003/0083686 A1 | 5/2003 | Freeman et al. |
| 2003/0109808 A1 | 6/2003 | Takinami et al. |
| 2003/0171699 A1 | 9/2003 | Brenneman |
| 2003/0187338 A1 | 10/2003 | Say et al. |
| 2004/0064068 A1 | 4/2004 | DeNuzzio et al. |
| 2004/116829 A1 | 6/2004 | Raney et al. |
| 2004/0127818 A1 | 7/2004 | Roe et al. |
| 2004/0171968 A1 | 9/2004 | Katsuki et al. |
| 2004/0186394 A1 | 9/2004 | Roe et al. |
| 2004/0236251 A1 | 11/2004 | Roe et al. |
| 2005/0038357 A1 | 2/2005 | Hartstein et al. |
| 2005/0251064 A1 | 11/2005 | Roe |

FOREIGN PATENT DOCUMENTS

| | | | |
|---|---|---|---|
| EP | 1411352 | * | 4/2004 |
| JP | 05073975 A | | 3/1993 |
| JP | 2000-116768 A2 | | 4/2000 |
| WO | WO 93/09710 A1 | | 5/1993 |
| WO | WO 93/09723 | | 5/1993 |
| WO | WO 01/72220 A1 | | 10/2001 |
| WO | WO 02/36010 A1 | | 5/2002 |
| WO | WO 02/056751 A2 | | 7/2002 |
| WO | WO 03006980 | * | 1/2003 |

OTHER PUBLICATIONS

U.S. Appl. No. 10/767,522, Jan. 29, 2004, Roe et al.
European Patent Application No. EP 05 745 633.7 Preliminary Report on Patentability mailed Mar. 3, 2009.

* cited by examiner

INTEGRATED DISPOSABLE FOR AUTOMATIC OR MANUAL BLOOD DOSING

CROSS REFERENCE TO RELATED APPLICATION

This application is a continuation of U.S. patent application Ser. No. 10/840,931 filed May 7, 2004, now U.S. Pat. No. 7,322,942 which is hereby incorporated by reference in its entirety.

BACKGROUND

The present invention generally relates to lancets used in bodily fluid sampling devices and more particularly, but not exclusively, to an integrated sampling device that contains multiple openings to allow fluid to be automatically or manually sampled.

A variety of body fluid sampling devices, such as blood glucose meters, have been developed to form an incision and to analyze body fluid from the incision. In one type of device, a lancet is used to form an incision, and after forming the incision, the user manually places a test strip against the skin in order to draw a fluid sample into the test strip. Sometimes the fluid drawn onto the test strip is not enough to generate accurate test results. Coagulation of blood or other fluids in the test strip can prevent further dosing of the test strip. When this occurs, the user has to discard the test strip and either try to collect additional fluid from the same incision onto a new test strip or form a second incision so as to repeat the process. As should be appreciated, this can be both wasteful and painful. Although test strips have been developed to test the sufficiency in the amount of the body fluid drawn, the sufficiency test occurs after the test strip draws the fluid, which is too late, because the test strip still has to be discarded.

Thus, there is need for further contribution in this area of technology.

SUMMARY

One aspect of the present invention concerns an integrated sampling device for analyzing body fluid. The device includes a sampling portion that defines a channel with a first opening. A test media is positioned along the channel for analyzing the body fluid. The sampling portion defines a second opening that is positioned closer to the test media than the first opening for dosing the body fluid onto the test media via the second opening when dosing of the body fluid via the first opening is unsuccessful.

Another aspect concerns a method in which body fluid is drawn into a first opening of a sampling device. The sampling device includes a channel to transport the body fluid onto test media. The body fluid drawn into the first opening is determined to be insufficient. The body fluid is collected with a second opening of the sampling device that is positioned closer to the test media than the first opening.

A further aspect concerns an integrated sampling device that includes means for forming an incision in skin and means for collecting body fluid automatically from the incision. The device further includes means for collecting the body fluid manually from the incision upon failure to collect the body fluid automatically, and means for analyzing the body fluid that is collected.

DESCRIPTION OF THE SELECTED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations, modifications, and further applications of the principles of the present invention as illustrated are contemplated as would normally occur to one skilled in the art to which the invention relates.

The present application generally relates to an integrated sampling device that has two openings for the drawing of bodily fluids. One opening is operatively coupled to a channel to automatically draw fluid through the channel up to a test strip or other test media to analyze the fluid. If the channel fails to draw a sufficient amount of fluid, a second opening is provided directly opposite or to the side of the test strip so the user may apply the sample fluid manually from the incision site through the second opening. The two openings insure that a test strip is not wasted and a new incision does not have to be formed.

Figure 1:
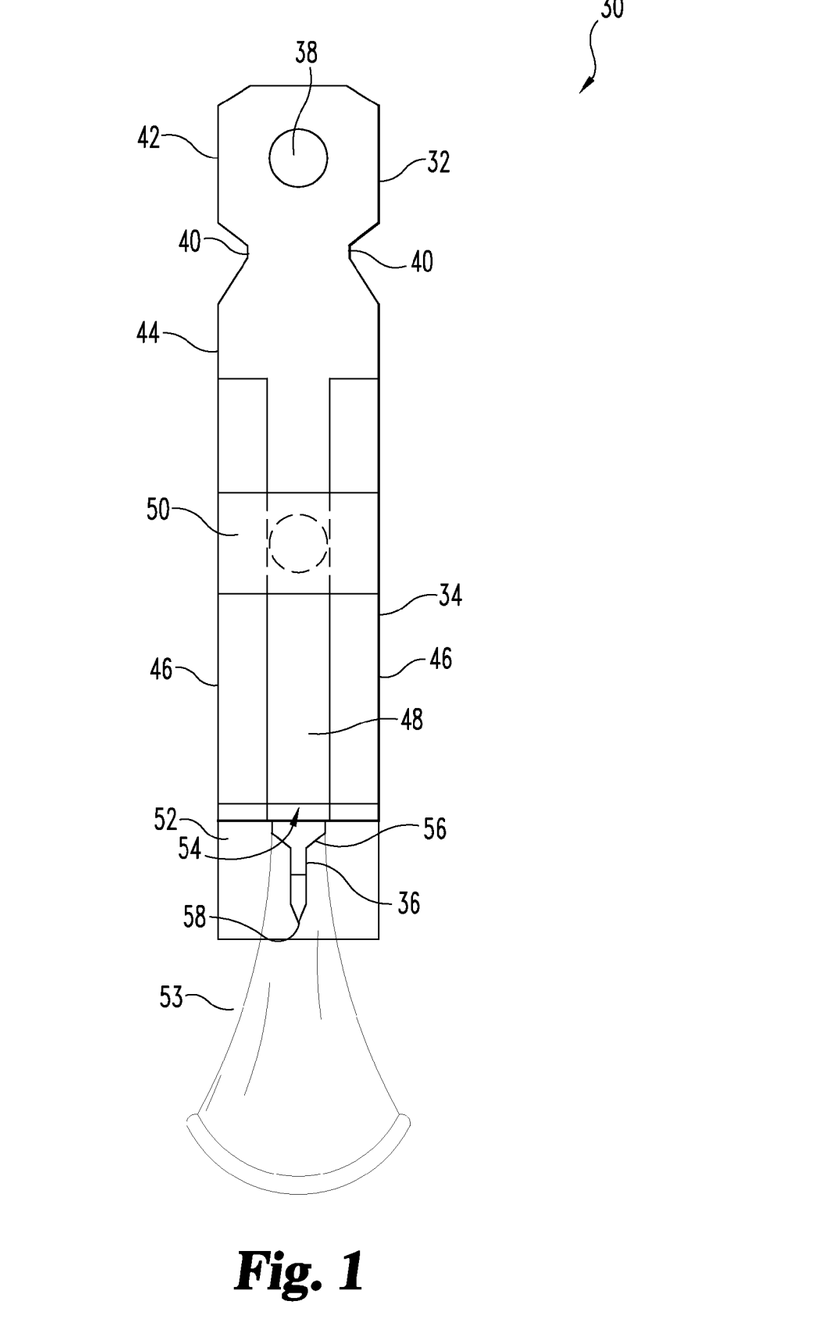
FIG. 1 is a front view of an integrated sampling device according to one embodiment of the present invention.

Referring now to FIG. 1, an integrated sampling device 30 according to one embodiment is illustrated. Overall, the flat design of device 30 aids in improving the manufacturability of the device 30. Moreover, the flat design allows multiple sampling devices 30 to be connected together for use in a cartridge, such as reel to reel type cartridge or a drum in an ACCU-CHEK® ADVANTAGE® brand meter (Roche Diagnostics Corporation, Indianapolis, Ind.). However, it should be appreciated that the integrated sampling device 30 can have a different overall shape in other embodiments. For example, it is envisioned that the device 30 in other embodiments can be round or cylindrical in shape. The integrated sampling device 30 includes a connection portion 32 for connecting the integrated sampling device 30 to a bodily fluid sampling device, a sampling portion 34 for drawing fluid from the incision site up for analysis, and an incision portion 36 for creating an incision in the body part to be sampled. The integrated sampling device 30 as illustrated is designed to be used with a variety of bodily fluid sampling devices. Moreover, the integrated sampling device 30 in the illustrated embodiment is intended to be disposed after one use for sanitary reasons. It is contemplated, however, that in other embodiments the integrated sampling device 30 can be used multiple times after sterilizing between uses. As shown, the connection portion 32 includes a connection loop 38 that is separated from the sampling portion 34 by notches 40. The notches 40 enable a firing mechanism of a bodily fluid sampling device to be attached to the integrated sampling device 30. The connection loop 38 defines a registration opening 42 that is designed to position and secure the integrated sampling device 30 to the bodily fluid sampling device.

The sampling portion 34 includes a body portion 44, spacer members 46, a capillary channel or cavity 48, a test media 50 and a collection sheet 52. The body portion 44 provides a support for the remaining parts of the sampling portion 34 and allows all of the different parts to be mounted thereupon. The spacer members 46 define the channel 48 through which fluid is drawn up to the test media 50 for testing. The collection sheet 52 further assists in defining the channel 48.

In the illustrated embodiment, the body portion 44 is formed from a metal lancet. It is contemplated that in other embodiments the body portion 44 can be formed of a high-strength plastic, a composite material, a combination thereof, or other materials readily apparent to one skilled in the art. By being substantially flat, the body portion 44 and other components can be easily formed from sheets of material, such as metal or plastic, and these sheets can be sandwiched together in order to mass produce body portions 44 and other components. Nonetheless, it should be appreciated that the body portion 44 can be shaped differently in alternate embodiments.

The spacer members 46 are made of plastic in the illustrated embodiment. It should be understood that the spacer members 46 can be formed from other materials, such as a bead of adhesive or a piece of metal, to name a few. In one embodiment, the spacer members 46 are coated with an adhesive on one side to fix the spacer members 46 to the body portion 44. In an alternate embodiment, the spacer members 46 are fixed to the body portion 44 using adhesive tape. Moreover, it is contemplated that the spacer members 46 may be secured in other manners readily apparent to one skilled in the art. In other embodiments, the body portion 44 and the spacer members 46 are directly attached to one another.

As shown, the channel 48 in the illustrated embodiment is a rectangularly shaped passage. It is contemplated that in other embodiments that this passage defines a different geometrical shape. One example, among others, would be a passage that is cylindrical in nature. The dimensions of the channel 48 vary in differing embodiments. FIG. 1 illustrates an embodiment where the channel 48 is sized to draw bodily fluid via capillary action. Alternate embodiments contemplate drawing fluid in other manners, such as via a vacuum.

Referring to FIG. 1, the test media 50 in the illustrated embodiment is located at the end of the channel 48 that is opposite the incision portion 36. However, it should be understood that the test media 50 can be located at difference locations along the channel 48. The test media 50 is configured to determine analyte levels or other properties of the body fluid sample. As should be appreciated, the properties of the body fluid sample can be determined through the chemical, electrical, electrochemical and/or optical properties of the bodily fluid sample collected on the test media 50 to name a few. For example, the test media 50 is illustrated as a chemically reactive reagent test strip. Optionally, an absorbent pad may be placed between the test strip in the closed end of the capillary channel 48 for wicking body fluid onto the test media 50. The spreading or wicking layers ensure that the fluid is adsorbed uniformly across the surface of the test media 50. The uniform application of the fluid assists the test media 50 in functioning properly. Fluid drains from the capillary into the wick material and spreads across the test media 50 for analysis. In one embodiment where the test media 50 is disposed within the capillary channel 48 no absorbent pad may be needed because the test strip will be in direct contact with the body fluid. In one form, the bodily fluid is blood and the property test is the level of glucose in the blood. Other embodiments contemplate test media 50 that measure other qualities of the bodily fluid. One nonlimiting example would be the pH level of blood or interstitial fluid.

As depicted in FIG. 1, the collection sheet 52 defines one side of the channel 48. In the illustrated embodiment, the collection sheet 52 is a section of a clear plastic sheet. The collection sheet 52 is a flexible sheet in the illustrated embodiment. By being flexible, the collection sheet 52 is able to deform during lancing, and yet is able to contact the skin without closing the incision in order to wick the fluid from the incision into the integrated sampling device 30. Moreover, collection sheet 52 provides a visual indicator such that the user can see whether the integrated sampling device 30 is positioned close enough to collect the fluid. In one particular form, collection sheet 52 is a transparent plastic film so as to allow the user to visualize the incision and the droplet of fluid during sampling. Other embodiments use different materials and colors of material to form the collection sheet 52. As should be appreciated, in other embodiments, the collection sheet 52 can be semi-transparent and/or opaque. The collection sheet 52 has a sampling end portion 53 that is configured to contact the skin during sampling. The sampling end portion 53 flexes during collection of fluid so that only a minimal amount of force is applied to the skin such that the fluid flow from the incision is not restricted. In one embodiment, the flow of fluid may be enhanced by forming the spacer members 46 and the collection sheet 52 out of a material that is hydrophilic, that has been treated to be hydrophilic, or that has been coated with a hydrophilic material such as a surfactant or hydrophilic polymers. The surfaces can also be treated using polyamides, oxidation (e.g. corona/plasma treatment); plasma chemical vapor deposition; vacuum vapor deposition of metals, metaloxides or non-metaloxides; or deposition of an element that oxidizes with water. In one form, the collection sheet 52 also protects the test media 50 from external disrupting conditions.

Figure 3:
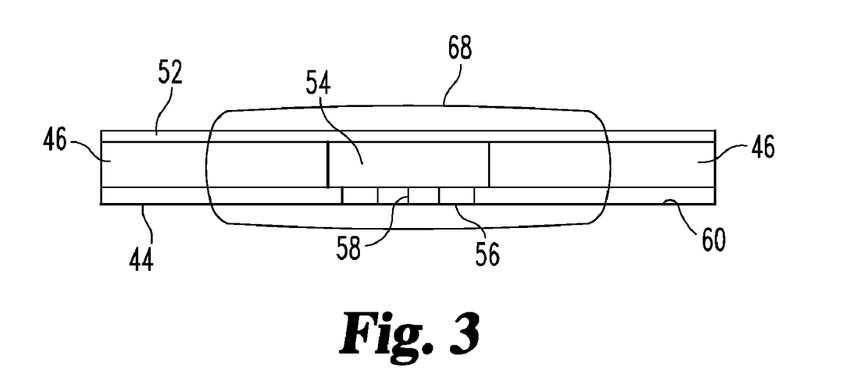
FIG. 3 is an enlarged end view of the integrated sampling device illustrated in FIG. 1.

With reference to FIG. 3, near the incision portion 36, the channel 48 has a first opening 54 through which the body fluid enters the capillary channel 48. By being located next to the incision portion 36, the first opening 54 is able to automatically draw body fluid from the incision, once the incision is formed. As illustrated, the sampling end portion 53 of the collection sheet 52 extends next to the first opening 54 such that the collection sheet 52 is able to assist in automatically drawing fluid into the first opening 54.

As mentioned before, the body portion 44 as well as the incision portion 33 in the illustrated embodiment is made from a flat lancet. As illustrated in FIG. 1, the incision portion 36 includes a blade support 56 and a blade 58 for forming an incision in a body part. Further, the body portion 44 includes a stop edge 60 at the end illustrated in FIG. 3. The blade support 56 connects the blade 58 to the body portion 44, and the blade support 56 is shaped to spread the strain that is placed on the blade 58. As depicted, the blade support 56 converges inwards to eventually form the sides of the blade 58. The blade 58 is sharp so it can form an incision in the skin, and the stop edge 60 can be used to limit the penetration depth of the blade 58. However, other types of mechanisms can be used to limit the penetration depth of the blade 58 before the skin reaches the stop edge 60. In the illustrated embodiment, the blade 58 has a cross sectional shape that is rectangular, but the blade 58 can be shaped differently in other embodiments. For example, the blade 58 has a circular cross sectional shape in one embodiment, and the blade 58 has a slanted shape in an alternate embodiment. Other configurations of the blade 58 readily apparent to those skilled in the art are contemplated. Moreover, even though the blade 58 is shown as being fixed in position with respect to the rest of the device 30, it should be appreciated that the blade 58 in other embodiments can be moveable with respect to the rest of the device 30. Although the integrated sampling device 30 in FIG. 1 uses the blade 58 to form an incision, it should be appreciated that the device 30 can incorporate other means for rupturing the skin, such as a laser.

Figure 2:
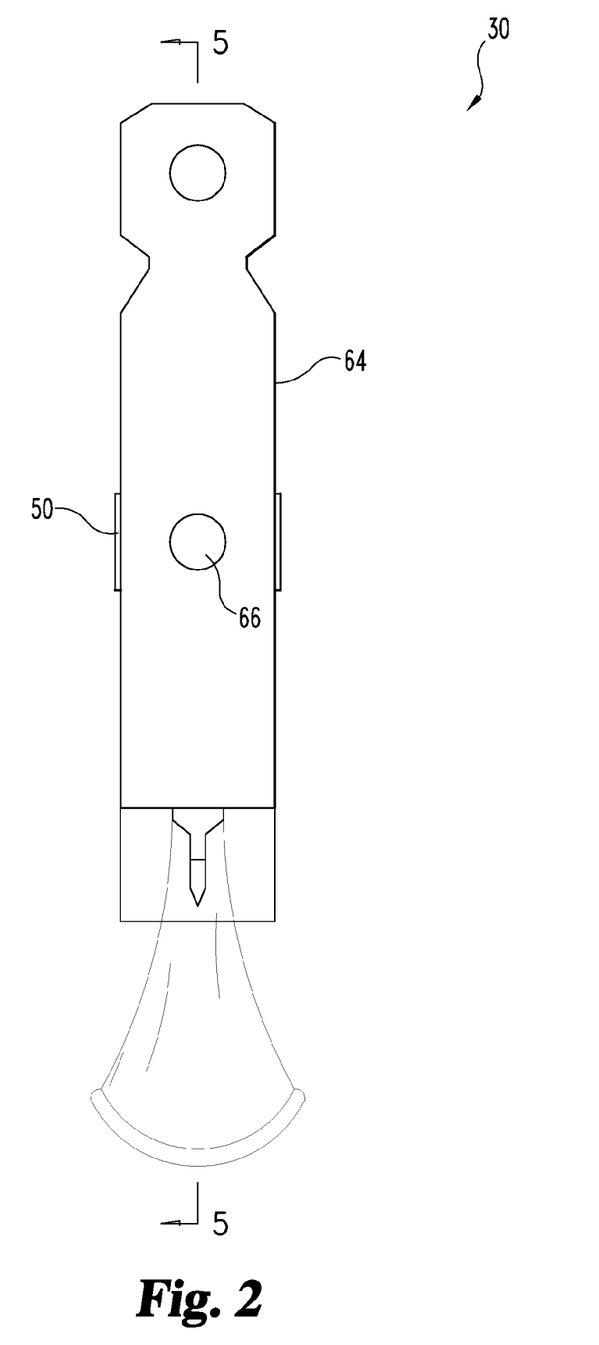
FIG. 2 is a rear view of the integrated sampling device depicted in FIG. 1.

Referring to FIG. 2, the body portion 44 of the integrated sampling device 30 includes a contact or expression surface 64 that defines a second opening 66 for manually dosing onto the test media 50. In the illustrated embodiment, the second opening 66 is machined into a lancet, but it should be appreciated that the second opening can be formed in other ways, such as through photo-etching. The second opening in FIG. 2 is generally circular in shape. However, the second opening can be shaped differently in other embodiments. As shown, the second opening 66 is positioned over the test media 50 to ensure the body fluid is directly applied to the test media 50. By positioning the second opening 66 directly over or near the test media 50, lesser amounts of fluid are required because the fluid does not have to fill the entire channel 48 before being deposited onto the test media 50. Although the second opening 66 in the illustrated embodiment is positioned directly over the test media 50, it is contemplated that in alternative embodiments, the second opening 66 can be placed partially over the test media 50 or to the side of the test media 50. When the body fluid is sampled through the first opening 54, the second opening 66 acts as a vent to vent air from the channel 48. In contrast, when fluid is sampled through the second opening 66, the first opening 54 can act as a vent. Nevertheless, it should be appreciated that vents can be formed at other locations in the integrated sampling device 30. For instance, a vent can be formed by the channel 48 at the end opposite the incision portion 36. To prevent accidental cuts, a protective cap 68 covers the blade 58, as is shown in FIG. 3. The protective cap 68 also ensures the sterility of the blade 58 before it is used to form an incision.

Figure 4:
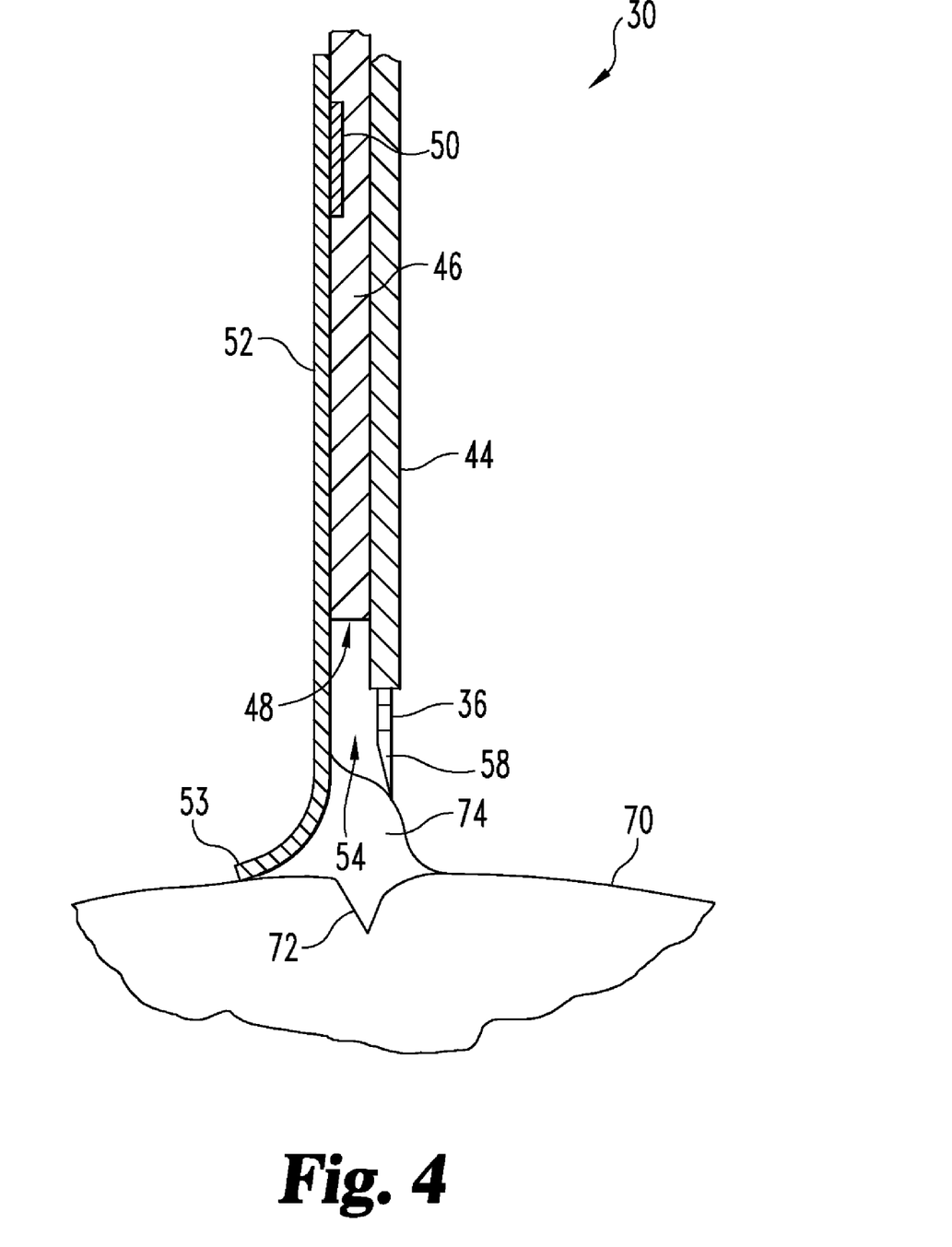
FIG. 4 shows fluid being sampled through the first opening of the FIG. 1 integrated sampling device.

A technique for sampling and analyzing body fluid with the integrated sampling device 30 will now be described with reference to FIGS. 4 and 5. As noted above, the integrated sampling device 30 samples fluid in two different ways. First, fluid is automatically sampled for analysis via the first opening 54 of the channel 48. If an insufficient amount of fluid is collected to allow analysis, the body fluid is then sampled manually via the second opening 66. Before fluid is collected with the second opening 66, additional fluid can be expressed by pressing the second opening around the incision, if needed.

Before forming an incision, the integrated sampling device 30 is installed into a body fluid sampling device that is able to fire device 30 into the skin to form an incision 72. In one embodiment, the body part in which the incision is formed is a finger, and in another embodiment, the body part is the forearm. It is contemplated, however, that fluid can be drawn from other body parts. Once fired the blade 60 penetrates the skin to form the incision, and afterwards, the blade 58 is retracted either fully or partially from the incision 72. The integrated sampling device 30 can be retracted from the incision 72 either manually by the user, or automatically through a retraction mechanism, such as a spring. Furthermore, the user in other embodiments can manually cut the skin with the blade 58 in order to form the incision. In the embodiment illustrated in FIG. 4, the blade 58 is fully retracted from the incision 72 to allow bodily fluid 74 to flow from the incision 72.

After lancing, the integrated sampling device 30 is positioned proximal to the body part 70 in order to collect fluid 74 from the incision 72. As should be appreciated, the integrated sampling device 30 simplifies positioning for collecting fluid 74. The integrated sampling device 30 does not have to be reoriented or repositioned after lancing in order to collect the fluid 74. Moreover, the collection sheet 52 provides a visual indicator to the user so as to ensure that the integrated sampling device 30 is positioned at the appropriate distance from the body part 70 for drawing fluid 74 from the incision 72. As depicted, the collection sheet 52 is longer than the blade 58 so that during fluid collection the collection sheet 52 is able contact the body part 70. In other embodiments, the collection sheet may be shorter than the blade or even the same length as the blade. Due to its flexible nature, the collection sheet 52 does not substantially compress the body part 70 such that the fluid 74 flow from the incision 72 is not restricted. In the illustrated embodiment, the collection sheet 52 contacts the body part 70 when fluid 74 is drawn. However, it is contemplated that the collection sheet 52 in other embodiments can be positioned slightly away so as to not contact the body part 70, but still close enough to draw the fluid 74. The hydrophilic qualities of the collection sheet 52 enhance the fluid flow along the collection sheet 52 and into the channel 48. As depicted in FIG. 4, body fluid 74 is drawn into the channel 48 via the first opening 54, and the drawn fluid 74 is transported to the test media 50. The fluid 74 can then be analyzed with the test media 50 in order to determine the desired property, such as selected analyte levels in the fluid 74.

Sometimes the amount of fluid 74 that bleeds (or is expressed) from the incision 72 is insufficient to fill the channel 48 such that the test media 50 is unable to provide accurate test results. By looking through the collection sheet 52, the user can visually determine whether or not a sufficient amount of fluid was drawn into the channel 48. In other embodiments, the integrated sampling device 30 can incorporate sensors, such as electrodes, that detect the sufficiency of the fluid sample. As previously mentioned, the integrated sampling device 30 incorporates the second opening 66, which allows a second opportunity for the body fluid 74 to be dosed onto the test media 50. The body fluid 74 can be dosed a second time after additional fluid 74 bleeds from the incision 72 and/or after the user expresses additional fluid from the incision 72, either manually or automatically. For example, the user can press the expression surface 64 against the body part 70 to force fluid out of the incision 72 and into the second opening 66. Since the second opening 66 is positioned closer to the test media 50 as compared to the first opening 54, the amount of fluid that must be drawn is significantly lower than the amount of fluid that has to be drawn up the channel 48.

Figure 5:
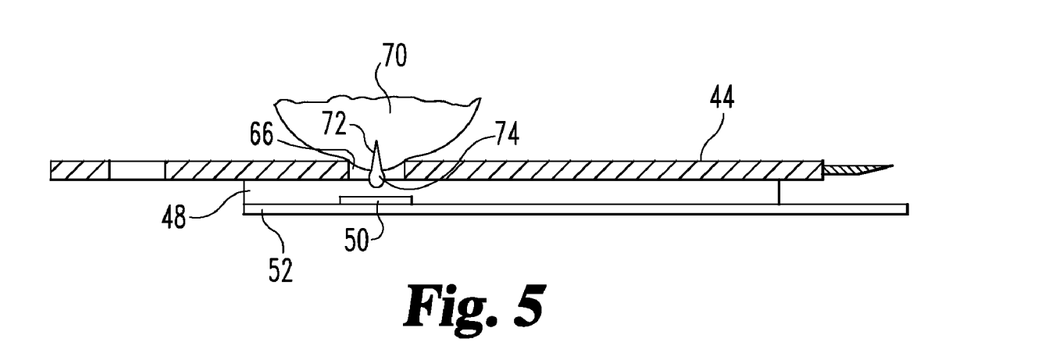
FIG. 5 shows the FIG. 1 integrated sampling device sampling fluid through the second opening.

FIG. 5 illustrates the integrated sampling device 30 during manual dosing of the fluid 74 through the second opening 66. Although dosing the body fluid 74 via the second opening 66 will be described with respect to manual dosing, it is contemplated that the dosing can also occur automatically. In the illustrated embodiment, the user detaches the integrated sampling device 30 from the firing mechanism of the body fluid sampling device to sample fluid 74 via the second opening 66, but it should be understood that the device 30 can remain attached to the body fluid sampling device before dosing through the second opening 66 in other embodiments. The user can allow the body fluid 74 to naturally bleed from the incision 72 before sampling the fluid via the second opening 66. Alternatively or additionally, to increase the amount of body fluid 74, the user can express additional body fluid 74 from the incision 72. In the illustrated embodiment, the user presses the expression surface 64 that surrounds the second opening 66 around the incision 72. The manual compression of the body part 70, such as a finger, forces the body fluid 74 out of the incision 72 and into the second opening 66. The body fluid 74 is then directly deposited onto the test media 50, and the test media 50 is then used to analyze the fluid sample.

Figure 6:
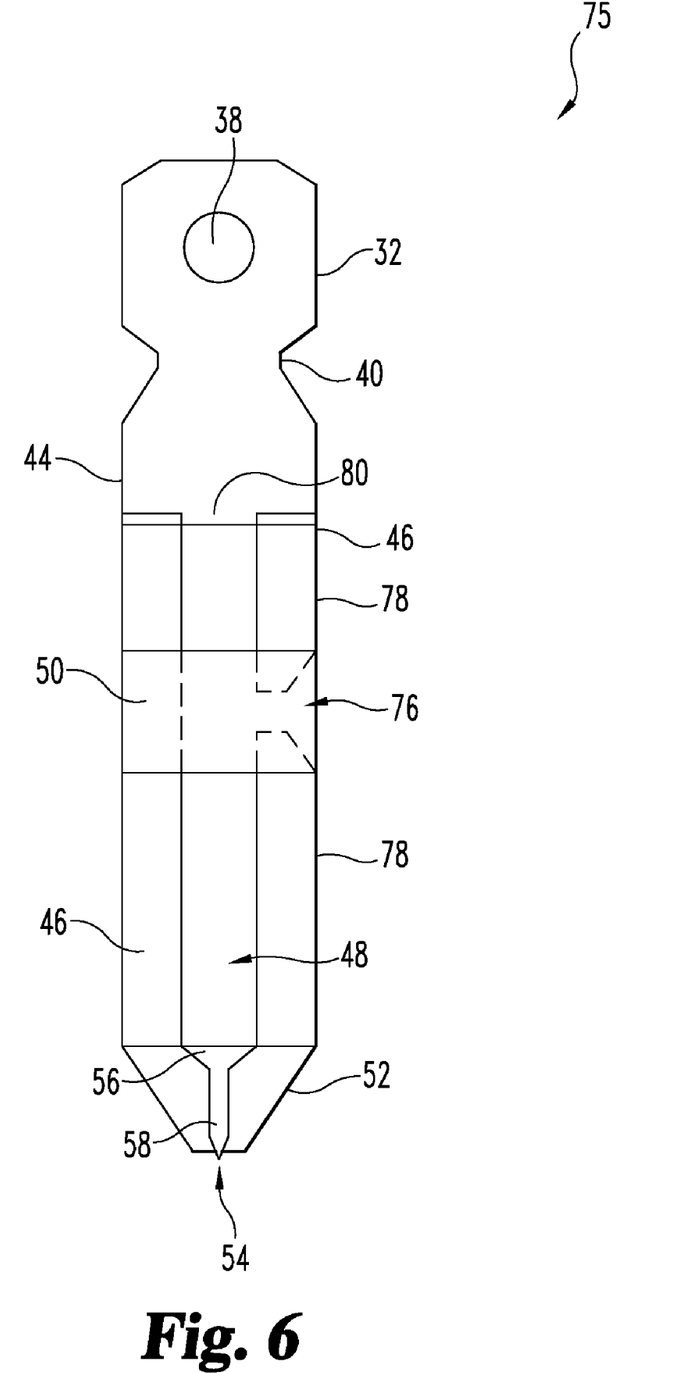
FIG. 6 is a front view of an integrated sampling device according to another embodiment.

An integrated sampling device 75 according to another embodiment is illustrated in FIG. 6. As shown, the sampling device 75 in FIG. 6 shares a number of features in common with the one described above, such as the channel 48, test media 50, collection sheet 52, first opening 54, and blade 58. However, instead of having a second opening formed in the body portion 44 of the sampling device 75, one of the spacers 46 defines a second opening 76 through which body fluid 74 can be collected onto the test media 50. In particular, the spacer 46 on the right lateral side of the sampling device 75, as viewed in FIG. 6, includes opposing spacer elements 78 that together define the second opening 76 along with the test media 50 and the body portion 44. Similar to the previous embodiment, the spacers 46 further define a vent opening 80 for venting air from the channel 48 at the end of the channel 48 opposite the first opening 54. Although the second opening 76 is formed in the spacer 46 at the right side in FIG. 6, it should be appreciated that the second opening 76 can be formed in either lateral side or in both lateral sides of the sampling device 75, however. Like before, the second opening 76 can be used to manual dose fluid 74 onto the test media 50 if an insufficient amount of fluid 74 is drawn via the first opening 74. As depicted, the sides of the second opening 76 are tapered so as to minimize dose hesitation when the fluid is sampled. In the illustrated embodiment, the second opening 76 is completely covered by the test media 50, but it is envisioned that the second opening 76 can be offset from the test media 50 in other embodiments. By forming the second opening 76 in one of the spacers 76, manufacturing of the integrated sampling device 75 can be simplified.

Figure 7:
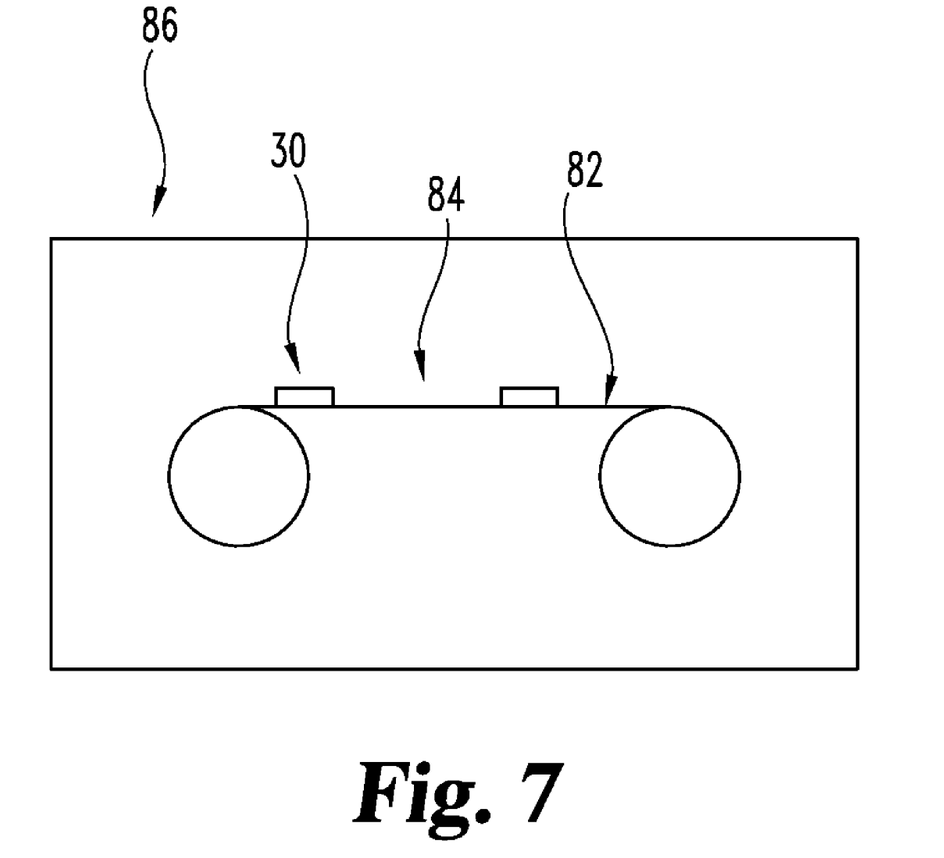
FIG. 7 is a diagrammatic view of a tape cassette storing the integrated sampling devices according to FIG. 1.

In the above described embodiments, only individual integrated sampling devices were shown, but it should be appreciated that these sampling devices can be incorporated into a drum or cassette such that multiple integrated sampling devices can be used together. For example, multiple integrated sampling devices (30) can be coupled together with a flexible sheet (82) so as to form a belt or tape (84) that can be stored in a reel-to-reel type cassette (86). Moreover, it is envisioned that the second opening can be formed at other locations on the integrated sampling device, and the sampling devices can include more than two openings through which fluid can be sampled. Although the integrated sampling devices in the drawings have two or more spacers, it should be understood that the sampling devices can include just a single spacer.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An integrated sampling device for analyzing body fluid, comprising:
   a sampling portion defining a channel with a first opening;
   a test media positioned along said channel for analyzing the body fluid;
   wherein said sampling portion defines a second opening that is positioned closer to said test media than said first opening for dosing the body fluid onto said test media via said second opening when dosing of the body fluid via said first opening is unsuccessful;
   a lancet with a blade that extends from said first opening;
   at least two spacers on said lancet defining opposite lateral sides of said channel, wherein said second opening is defined in at least one of said two spacers;
   wherein said at least two spacers are sandwiched between said lancet and said test media;
   wherein said test media covers one side of said second opening so that said second opening opens along said lateral side of said channel at said test media;
   said sampling portion defining a vent opening at an end of the channel that is opposite the first opening; and
   the first opening, the second opening, and the vent opening are separate and distinct from one another.

2. The device of claim 1, further comprising a hydrophilic sheet extending proximal to said first opening for drawing the body fluid into said first opening.

3. The device of claim 2, wherein said hydrophilic sheet at the first opening has a trapezoidal shape.

4. The device of claim 1, further comprising a collection sheet extending proximal to said first opening for drawing the body fluid into said first opening.

5. The device of claim 1, wherein said sampling portion is generally flat.

6. The device of claim 1, wherein said sampling portion and said test media are incorporated into a cassette.

7. The device of claim 1, wherein said sampling portion includes:
   a collection sheet covering said two spacers, said collection sheet having a portion extending from said first opening for drawing fluid into said first opening.

8. The device of claim 7, wherein said collection sheet is transparent to allow determination of sufficiency of the body fluid in said channel.

9. The device of claim 7, wherein said channel is sized to draw the body fluid via capillary action.

10. The device of claim 1, wherein said second opening has tapered sides to minimize dose hesitation.

11. A method, comprising:
    forming an incision with a blade that extends from a sampling device;
    drawing body fluid from the incision into a first opening of the sampling device, wherein the sampling device includes a channel to transport the body fluid onto test media;
    determining that the body fluid drawn into the first opening is insufficient; and
    collecting the body fluid with a second opening of the sampling device that is positioned closer to the test media than the first opening, wherein the second opening is defined in a spacer located on one side of the sampling device, wherein said collecting includes facing the one side of the sampling device with the second opening towards the incision.

12. The method of claim 11, further comprising testing the body fluid with the test media.

13. The method of claim 11, further comprising expressing the body fluid from the incision before said collecting.

14. The method of claim 13, wherein said expressing includes pressing the sampling device against the skin.

15. The method of claim 11, wherein said drawing includes drawing the body fluid into the channel via capillary action.

16. The method of claim 11, wherein said determining includes visually determining that the body fluid drawn into the first opening is insufficient.

17. The method of claim 11, wherein said determining includes automatically determining that the body fluid drawn into the first opening is insufficient with a sensor in the sampling device.

18. The method of claim 11, further comprising:
  wherein the sampling device has opposing lateral side edges; and
  wherein the second opening opens at one of the lateral side edges.

19. An integrated sampling device for analyzing body fluid, comprising:
  a sampling portion defining a channel with a first opening;
  a test media positioned along said channel for analyzing the body fluid;
  wherein said sampling portion defines a second opening that is positioned closer to said test media than said first opening for dosing the body fluid onto said test media via said second opening when dosing of the body fluid via said first opening is unsuccessful;
  a lancet with a blade that extends from said first opening;
  at least two spacers on said lancet defining opposite sides of said channel, wherein said second opening is defined in at least one of said two spacers;
  wherein said sampling portion defines a vent opening at an end of the channel that is opposite the first opening; and
  wherein the first opening, the second opening and the vent opening are separate and distinct from one another.

20. The device of claim 19, further comprising a hydrophilic sheet extending proximal to said first opening for drawing the body fluid into said first opening.

21. The device of claim 20, wherein said hydrophilic sheet at the first opening has a trapezoidal shape.

22. The device of claim 20, wherein said hydrophilic sheet is transparent to allow determination of sufficiency of the body fluid in said channel.

23. The device of claim 19, wherein said second opening has tapered sides to minimize dose hesitation.

24. The device of claim 19, further comprising:
  wherein said at least two spacers are sandwiched between said lancet and said test media; and
  wherein said test media defines one side of said second opening so that said second opening opens along said channel at said test media.

* * * * *